United States Patent [19]

Ching et al.

[11] Patent Number: 5,780,308
[45] Date of Patent: Jul. 14, 1998

[54] CALIBRATION REAGENTS FOR SEMIQUANITATIVE BINDING ASSAYS AND DEVICES

[75] Inventors: ShanFun Ching, Libertyville; Julian Gordon, Lake Bluff, both of Ill.

[73] Assignee: Abbott Laboratories, Abbott Park, Ill.

[21] Appl. No.: 854,785

[22] Filed: May 12, 1997

Related U.S. Application Data

[60] Continuation of Ser. No. 395,139, Feb. 27, 1995, abandoned, which is a division of Ser. No. 81,063, Jun. 22, 1993, abandoned, which is a continuation of Ser. No. 823,486, Jan. 22, 1992, abandoned.

[51] Int. Cl.$^6$ .................................................. G01N 33/558
[52] U.S. Cl. .................. 436/514; 436/524; 436/528; 436/538; 436/540; 436/541; 436/65; 435/5; 435/7.1; 435/7.92; 435/970; 435/971; 422/55; 422/56
[58] Field of Search ........................... 435/5, 7.1, 7.92, 435/970, 971; 436/514, 524, 528, 538, 540, 541, 65; 422/55, 56

[56] References Cited

U.S. PATENT DOCUMENTS

| | | | |
|---|---|---|---|
| 3,802,842 | 4/1974 | Lange et al. | 23/253 TP |
| 3,915,639 | 10/1975 | Friedenberg | 23/230 B |
| 4,059,407 | 11/1977 | Hochstrasser | 23/253 TB |
| 4,094,647 | 6/1978 | Deutsch et al. | 23/253 TP |
| 4,168,146 | 9/1979 | Grubb et al. | 23/230 B |
| 4,235,601 | 11/1980 | Deutsch et al. | 23/230 R |
| 4,361,537 | 11/1982 | Deutsch et al. | 422/56 |
| 4,366,241 | 12/1982 | Tom et al. | 435/7 |
| 4,378,428 | 3/1983 | Farina et al. | 435/7 |
| 4,435,504 | 3/1984 | Zuk et al. | 435/7 |
| 4,536,479 | 8/1985 | Vander-Mallie | 436/537 |
| 4,551,308 | 11/1985 | Mintz | 422/58 |
| 4,594,327 | 6/1986 | Zuk | 436/514 |
| 4,689,309 | 8/1987 | Jones | 436/95 |
| 4,703,017 | 10/1987 | Campbell et al. | 436/501 |
| 4,740,468 | 4/1988 | Weng et al. | 435/7 |
| 4,757,004 | 7/1988 | Houts et al. | 435/7 |
| 4,806,311 | 2/1989 | Greenquist | 422/56 |
| 4,806,312 | 2/1989 | Greenquist | 422/56 |
| 4,861,711 | 8/1989 | Friesen et al. | 436/7 |
| 4,868,108 | 9/1989 | Bahar et al. | 436/7 |
| 4,879,215 | 11/1989 | Weng et al. | 435/7 |
| 4,943,522 | 7/1990 | Eisinger et al. | 435/7 |
| 4,952,517 | 8/1990 | Bahar | 436/518 |
| 4,956,275 | 9/1990 | Zuk et al. | 435/7 |
| 4,956,302 | 9/1990 | Gordon et al. | 436/161 |
| 4,960,691 | 10/1990 | Gordon et al. | 435/6 |
| 5,089,391 | 2/1992 | Buechler et al. | 435/7.1 |
| 5,395,754 | 3/1995 | Lambotte et al. | 435/607.4 |
| 5,480,792 | 1/1996 | Buechler et al. | 435/6 |

FOREIGN PATENT DOCUMENTS

| | | |
|---|---|---|
| 088 636 | 9/1983 | European Pat. Off. . |
| 271 204 | 6/1988 | European Pat. Off. . |
| 284 232 | 9/1988 | European Pat. Off. . |
| 2 204 398 | 11/1988 | United Kingdom . |
| WO 86/03839 | 7/1986 | WIPO . |

OTHER PUBLICATIONS

Zuk, et al., *Clin. Chem.*, "Enzyme Immunochromatography—A Quantitative Immunoassay Requiring No Instrumentation", 31(7):1144–1150 (1985).

*Primary Examiner*—Jeffrey Stucker
*Attorney, Agent, or Firm*—David L. Weinstein

[57] ABSTRACT

The novel analytical devices and methods of the present invention involve a semiquantitative specific binding assay method for the detection of the presence of at least a predetermined minimum concentration of an analyte in the test sample. A calibration reagent is present at a concentration sufficient to inhibit the formation of a detectable analyte complex unless a predetermined minimum concentration of analyte is present in the test sample.

9 Claims, 5 Drawing Sheets

CALIBRATION REAGENTS FOR SEMIQUANITATIVE BINDING ASSAYS AND DEVICES

This application is a continuation of application Ser. No. 08/395,139 filed on Feb. 27, 1995, now abandoned which is a division of U.S. application Ser. No. 08/081,063, filed on Jun. 22, 1993, now abandoned which is a continuation of U.S. application Ser. No. 07/823,486 filed Jan. 22, 1992, now abandoned.

BACKGROUND OF THE INVENTION

1. Field of the Invention

In general, the present invention relates to assay methods and devices for the detection and/or quantitation of an analyte in a test sample by means of a binding assay. In particular, the invention relates to novel assay methods and test devices in which a calibration reagent is used for the qualitative and semiquantitative detection of analyte.

2. Related Art

Various analytical procedures and devices are commonly employed in specific binding assays to determine the presence and/or amount of substances of interest or clinical significance which may be present in biological or non-biological fluids. Such substances are commonly termed "analytes" and can include antibodies, antigens, drugs, hormones, etc.

The ability to use materials which specifically bind to an analyte of interest has created a burgeoning diagnostic device market based on the use of binding assays. Binding assays incorporate specific binding members, typified by antibody and antigen immunoreactants, wherein one member of the specific binding pair is labeled with a signal-producing compound (e.g., an antibody labeled with an enzyme, a fluorescent compound, a chemiluminescent compound, a radioactive isotope, a direct visual label, etc.). For example, in a binding assay the test sample suspected of containing analyte can be mixed with a labeled anti-analyte antibody, i.e., conjugate, and incubated for a period of time sufficient for the immunoreaction to occur. The reaction mixture is subsequently analyzed to detect either that label which is associated with an analyte/conjugate complex (bound conjugate) or that label which is not complexed with analyte (free conjugate). As a result, the amount of label in one of these species can be correlated to the amount of analyte in the test sample.

The solid phase assay format is a commonly used binding assay technique. There are a number of assay devices and procedures wherein the presence of an analyte is indicated by the analyte's binding to a conjugate and/or an immobilized complementary binding member. The immobilized binding member is bound, or becomes bound during the assay, to a solid phase such as a dipstick, test strip, flow-through pad, paper, fiber matrix or other suitable solid phase material. The binding reaction between the analyte and the assay reagents results in a distribution of the conjugate between that which is immobilized upon the solid phase and that which remains free. The presence or amount of analyte in a test sample is typically indicated by the extent to which the conjugate becomes immobilized upon the solid phase material.

The use of reagent-impregnated test strips in specific binding assays is also well-known. In such procedures, a test sample is applied to one portion of the test strip and is allowed to migrate or wick through the strip material. Thus, the analyte to be detected or measured passes through or along the material, possibly with the aid of an eluting solvent which can be the test sample itself or a separately added solution. The analyte migrates into a capture or detection zone on the test strip, wherein a complementary binding member to the analyte is immobilized. The extent to which the analyte becomes bound in the detection zone can be determined with the aid of the conjugate which can also be incorporated in the test strip or which can be applied separately.

Examples of devices based upon these principles include the following patents and patent applications. Hochstrasser (U.S. Pat. No. 4,059,407) discloses a dipstick device which can be immersed in a biological fluid for a semi-quantitative analysis of the analyte in the fluid. The semi-quantitative analysis of the analyte is accomplished by using a series of reagent-containing pads wherein each pad in the series will produce a detectable color (i.e., a positive result) in the presence of an increasing amount of analyte. Also of interest in the area of dipstick devices are U.S. Pat. Nos. 3,802,842, 3,915,639 and 4,689,309.

An early test strip device is described by Deutsch et al. in U.S. Pat. Nos. 4,094,647, 4,235,601 and 4,361,537. In general, the device comprises a material capable of transporting a solution by capillary action, i.e., a wicking or chromatographic action. Different areas or zones in the test strip contain the assay reagents needed to produce a detectable signal as the analyte is transported to or through such zones. The device is suited for both chemical assays and binding assays and uses a developer solution to transport analyte along the strip.

Many alternatives to or variations on the Deutsch et al. device have been disclosed. For example, Tom et al. (U.S. Pat. No. 4,366,241) disclose a bibulous strip with an immunosorbing zone to which the test sample is directly applied and wherein the assay result is detected. Grubb et al. (U.S. Pat. No. 4,168,146) describe the use of a porous test strip material to which is covalently bound an antigen-specific antibody. In performing the assay, the test strip is immersed in a solution suspected of containing an antigen, and capillary migration of the solution through the test strip is allowed to occur. As the antigen moves through the test strip it binds to the immobilized antigen-specific antibody. The presence of antigen is then determined by wetting the test strip with a second antigen-specific antibody to which a fluorescent or enzyme label is covalently bound. Quantitative testing can be achieved by measuring the length of the strip that contains bound and lab antigen. Further variations on such a test strip are disclosed in U.S. Pat. Nos. 4,435,504 which employs a two enzyme indicator system; 4,594,327 which discloses the addition of a binding agent to whole blood samples to cause the red blood cells to aggregate at the area of the test strip adjacent to the air/liquid interface; and 4,757,004 which discloses a means for controlling the shape of the fluid front migrating along the test strip. Zuk et al., Enzyme Immunochromatography - A Quantitative Immunoassay Requiring No Instrumentation, *Clinical Chemistry*, 31(7): 1144–1150, 1985, further describe the assay principle.

Rosenstein (European Patent Office Publication No. 0 284 232) and Campbell et al. (U.S. Pat. Nos. 4,703,017) describe assay methods and devices for performing specific binding assays wherein the detectable label is a colored particle such as a liposome containing a dye. The labeled reagent is mixed with the test sample to form a test solution and is applied to an immobilized binding member for detection.

Weng, et al. (U.S. Pat. Nos. 4,740,468 and 4,879,215) describe another device and method for performing a specific binding assay. The assay involves both an immobile second binding member which binds to a mobile first binding member and an immobilized analog of the analyte which removes unbound first binding member from the assay system prior to its contacting the detection site. Greenquist, et al. (U.S. Pat. Nos. 4,806,311 and 4,806,312) describe a similar assay method device wherein a first immobilized reagent, such as an analyte-analog, is present in a reagent zone to remove free monovalent labeled-binding members from the assay system prior to the test samples contact with the detection layer reagents.

Bahar, et al. (U.S. Pat. No. 4,868,108) describe an assay method and device for performing specific binding assays, wherein the device involves both a multizoned support through which test sample is transported and the use of an enzyme/substrate detection means. Eisinger, et al. (U.S. Pat. No. 4,943,522) describe an assay method and a device for performing binding assays, wherein the device involves a multizoned non-bibulous lateral flow membrane through which test sample is transported to a binding zone.

Ullman, et al. (European Patent Application No. 87309724.0; Publication No. 0 271 204) is related to the previously discussed Weng, et al. patents. Ullman, et al. describe the preparation of a test solution which contains an analyte-analog and a test sample suspected of containing the analyte. The test solution is contacted to a bibulous material having two, sequential binding sites: the first binding site containing a specific binding pair member capable of binding the analyte and the analyte-analog, the second binding site capable of binding that analyte-analog which is not bound at the first binding site.

Cerny, E. (International Application No. PCT/US85/02534; Publication No. WO 86/03839) describes a binding assay wherein a test solution, containing test sample and labeled test substance, is allowed to diffuse through a solid phase. The assay provides a measurable diffusion pattern, wherein the pattern has a diameter which is greater than the diameter of the diffusion pattern for the labeled test substance alone.

Zuk, et al. (U.S. Pat. No. 4,956,275) describe a method and device for detecting an analyte by means of a sensor apparatus. An analyte-related signal is measured at two or more sites on the assay device by means of the sensor apparatus, and the mathematical relationship between the measurements provides a value (e.g., difference, ratio, slope, etc.) which is compared against a standard containing a known amount of analyte.

Further examples of specific binding assay devices include the following. Swanson et al. (EP 088 636) describe an apparatus for the quantitative determination of an analyte involving a fluid-permeable solid medium containing a predetermined number of successive spaced reaction zones. The reaction zones include a Ractant capable of reacting with the analyte to produce a detectable signal; the greater the number of zones producing a detectable signal, the greater the amount of analyte in the test sample. Friesen et al. (U.S. Pat. No. 4,861,711) describe a sheet-like diagnostic device containing several functional sectors through which the sample must pass. At least one of the sectors includes an immobilized reagent having a biological affinity for the analyte or an analyte complex.

Gordon et al. (U.S. Pat. No. 4,956,302) describe a teststrip device characterized by having the analyte, test sample and/or eluting solvent migrate through the device in a single direction, thereby sequentially contacting reagent-containing zones or detection zones. Gordon et al. (U.S. Pat. No. 4,960,691) describe a device that includes one or more established pathways which direct the migration of the analyte, test sample and/or eluting solvent through the reagent-containing zones and detection zones in a predetermined order.

In general, analyte detection with a specific binding assay having adequate sensitivity can be achieved using a sandwich assay format. Semiquantitative determinations, however, are difficult to perform with test samples containing low levels of analyte because of the incomplete capture of the analyte and labeled reagent upon the solid phase. Thus, there is a need for a specific binding assay format and device which permit the semiquantitative detection of analyte even when low levels of analyte are present in the test sample.

SUMMARY OF THE INVENTION

The present invention is directed to a multizone test device for semiquantitatively determining the presence of at least a predetermined minimum concentration of an analyte in a test sample. The device involves: a porous material containing, a soluble conjugate including a labeled specific binding member which directly or indirectly binds the analyte to form a labeled analyte complex; a capture reagent including an unlabeled specific binding member which is attached to the porous material and which binds the labeled analyte complex to form an immobilized labeled analyte complex; and a soluble calibration reagent including an unlabeled specific binding member which blocks the binding of the analyte to the capture reagent. The calibration reagent thereby controls the proportion of the analyte that binds to the capture reagent such that the analyte in the test sample must exceed a minimum concentration before the immobilized labeled complex is formed. The capture reagent is immobilized at a capture site wherein the immobilized labeled complex is separated from the test sample. The presence of label associated with the immobilized labeled complex is detected to determine the presence of at least a predetermined minimum concentration of an analyte in the test sample. It was unexpectedly discovered the the assay reagents could be simultaneously combined with the test sample and still provide the calibration effect.

In one embodiment of the present invention, the porous material involves a teststrip wherein the conjugate and the calibration reagent are contained in a reagent zone upstream from the capture site. In another embodiment, the reagent zone contains at least two reaction zones: a first reaction zone containing the calibration reagent and a second reaction zone containing the conjugate. In yet another embodiment, the conjugate indirectly binds the analyte by means of an ancillary specific binding member. In a further embodiment, the conjugate is a visually detectable particle coated with more than one analyte-specific binding member.

The calibration reagent is typically either an analyte-specific binding member or an analyte-analog. If the calibration reagent is an analyte-analog, then the analyte-analog may be a fragment of an analyte molecule or a synthetic analyte molecule. If the calibration reagent is an analyte-specific binding member, then the analyte-specific binding member may be an anti-analyte antibody or an anti-idiotypic antibody.

DETAILED DESCRIPTION OF THE INVENTION

Figure 1:
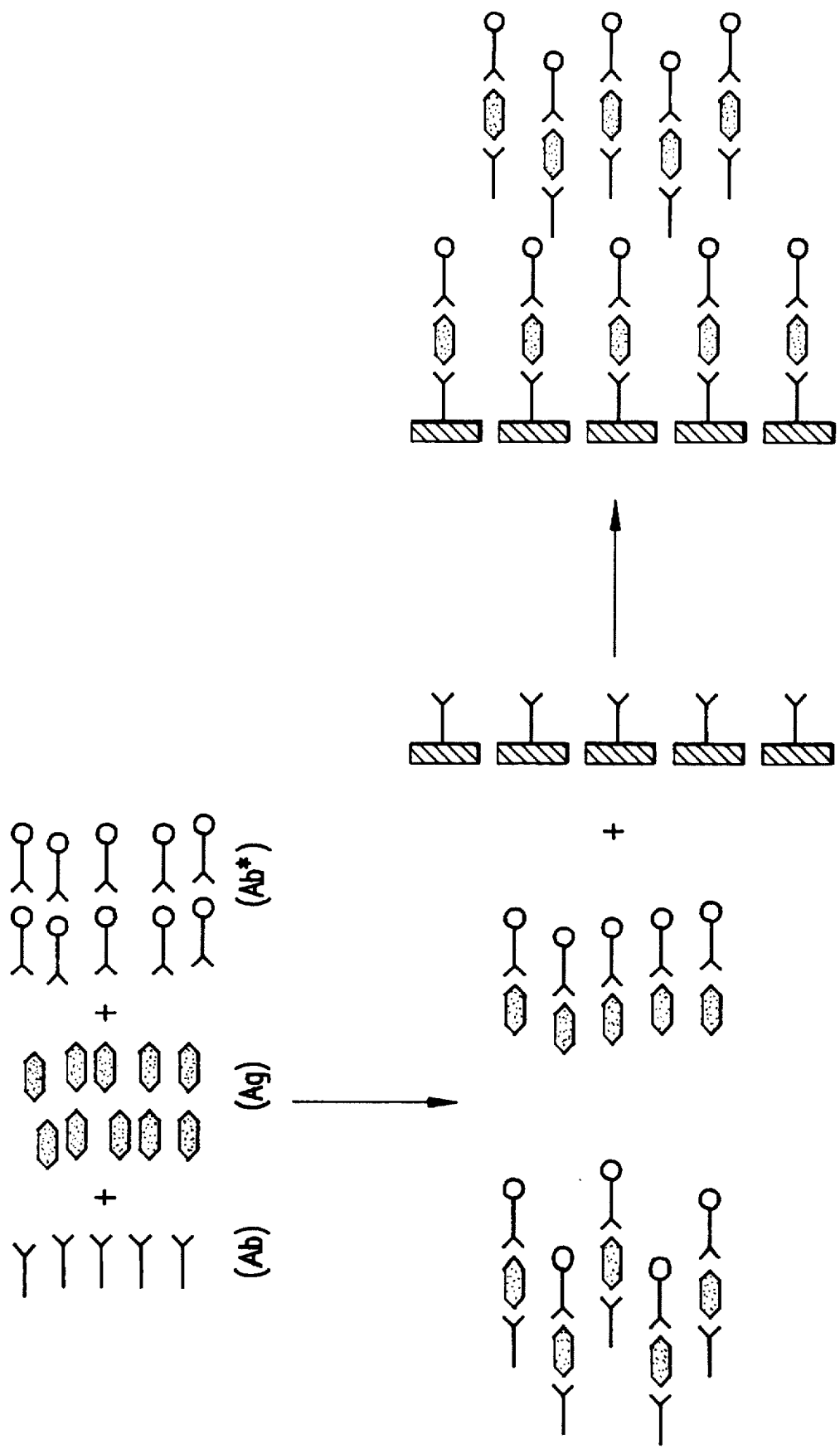
FIG. 1 depicts an antibody/antigen sandwich assay in accordance with the present invention.

The semiquantitative specific binding assay method of the present invention involves the detection of the presence of at least a predetermined minimum concentration of an analyte in the test sample. In one embodiment, the test sample is contacted with a labeled analyte-specific binding member and a calibration reagent which is also an analyte-specific binding member. The labeled binding member and calibration reagent are allowed to bind to the analyte thereby forming analyte complexes. The complexes are then contacted to an insoluble analyte-specific binding member which has been immobilized upon a solid phase. The subsequently immobilized, labeled analyte complexes can then be detected. The analyte, however, will only bind to the solid phase when the amount of analyte in the test sample is sufficiently high to bind both the labeled analyte-specific binding member and the calibration reagent. In other words, the calibration reagent is present at a concentration sufficient to inhibit the formation of an immobilized, labeled analyte complex unless a predetermined minimum concentration of analyte is present in the test sample. If the analyte is present at a level above such minimum concentration, then an immobilized, labeled analyte complex is formed and detected, thereby allowing a determination of the presence of at least a predetermined minimum concentration of an analyte in the test sample.

Suitable labeled binding member/calibration reagent combinations for use in the present invention include the use of a labeled and unlabeled analyte-specific binding member. Typically, the unlabeled analyte-specific binding member or calibration reagent is the same as that analyte-specific binding member which is immobilized upon the solid phase. In another embodiment, the analyte-specific binding members may be selected from antibodies involving a labeled analyte-specific binding member in combination with an unlabeled anti-idiotypic antibody as the calibration reagent and a third analyte-specific binding member immobilized on the solid phase. In yet another embodiment, the labeled specific binding member and calibration specific binding member may be the same such that they compete for binding to the analyte. In this embodiment, the analyte must be present in a concentration that will bind the calibrator reagent and still be sufficient to form a detectable amount of analyte/labeled binding member complex.

As will be described in greater detail hereinafter, the semiquantitative assay devices of the present invention involve at least one capture or detection site. The capture site is incorporated with an immobilized reagent which is not capable of being solubilized or otherwise substantially removed from the site. In general, the immobilized reagent in the capture site is a binding member specific for the analyte which binds to the test sample analyte and thereby immobilizes the analyte and/or labeled analyte complex in the capture site. For example, a test solution can be made containing a soluble labeled binding member specific for the analyte, a soluble unlabeled binding member specific for the analyte and the test sample. The test solution may be formed in the device itself or in a separate container. The assay reagents bind to the analyte present in the test sample. The test solution is subsequently contacted to the assay device, and a detectable signal will appear at the capture site if the analyte concentration is sufficiently high so that analyte is present to bind both the labeled specific binding member and the unlabeled calibration reagent. In alternative embodiments, more than one capture site can be used such that the number of sites which contain a detectable signal is proportional to the analyte concentration in the test sample. Thus, semiquantitative detection can include the instrumental determination of analyte as well as a visual determination which provides a numerical value.

Before proceeding with the description of the various embodiments of the present invention, a number of terms used herein will be defined. "Test sample" refers to a material suspected of containing the analyte. The test sample can be used as obtained directly from the source or following a pretreatment so as to modify its character. The test sample can be derived from any source, such as a physiological fluid, including, blood, saliva, ocular lens fluid, cerebral spinal fluid, sweat urine, milk, ascites fluid, mucous, synovial fluid, peritoneal fluid, amniotic fluid or the like. Pretreatment may involve preparing plasma from blood, diluting viscous fluids, or the like. Methods of treatment can involve filtration, distillation, concentration, inactivation of interfering components, and the addition of reagents. Besides physiological fluids, other liquid samples can be used such as water, food products and the like for the performance of environmental or food production assays as well as diagnostic assays. In addition, a solid material suspected of containing the analyte can be used as the test sample once it is modified to form a liquid medium or to release the analyte.

"Specific binding member" refers to a member of a specific binding pair, i.e., two different molecules wherein one of the molecules specifically binds to the second molecule through chemical or physical means. In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog or a specific binding member made by recombinant techniques or molecular engineering. If the specific binding member is an immunoreactant it can be, for example, an antibody, antigen, hapten, or complex thereof. If an antibody is used, it can be a monoclonal or polyclonal antibody, a recombinant protein or antibody, a chimeric antibody, a mixture(s) or fragment(s) thereof, as well as a mixture of an antibody and other specific binding members. The details of the preparation of such antibodies and their suitability for use as specific binding members are well-known to those skilled-in-the-art.

"Analyte" or "analyte of interest" refers to the compound or composition to be detected or measured and which has at least one epitope or binding site. The analyte can be any substance for which there exists a naturally occurring analyte-specific binding member or for which an analyte-specific binding member can be prepared. Analytes include, but are not limited to toxins, organic compounds, proteins, peptides, microorganisms, amino acids, nucleic acids, hormones, steroids, vitamins, drugs (including those administered for therapeutic purposes as well as those administered for illicit purposes), and metabolites of or antibodies to any of the above substances. The term "analyte" also includes any antigenic substances, haptens, antibodies, macromolecules and combinations thereof.

"Analyte-analog" refers to a substance which cross-reacts with the analyte-specific binding member, although it may do so to a greater or a lesser extent than does the analyte itself. The analyte-analog can include a modified analyte as well as a fragmented or synthetic portion of the analyte molecule, so long as the analyte-analog has at least one epitopic site in common with the analyte of interest. An example of an analyte-analog is a synthetic peptide sequence which duplicates at least one epitope of the whole-molecule analyte so that the analyte-analog can bind to the analyte-specific binding member.

"Conjugate" refers to a substance comprising a detectable label attached to a specific binding member. The attachment may be covalent or non-covalent binding, but the method of attachment is not critical to the present invention. The label allows the conjugate to produce a detectable signal that is directly or indirectly related to the amount of analyte in the test sample. The specific binding member component of the conjugate is selected to directly bind to the analyte or to indirectly bind the al,alyte by means of an ancillary specific binding member, which is described in greater detail hereinafter. The conjugate can be incorporated into the test device at a site upstream from the capture site, it can be combined with the test sample to form a test solution, it can be added to the test strip or device separately from the test sample or it can be predeposited or reversibly immobilized at the capture site. In addition, the binding member may be labeled before or during the performance of the assay by means of a suitable attachment method.

"Label" refers to any substance which is capable of producing a signal that is detectable by visual or instrumental means. Various labels suitable for use in the present invention include labels which produce signals through either chemical or physical means. Such labels can include enzymes and substrates; chromogens; catalysts; fluorescent compounds; chemiluminescent compounds; radioactive labels; direct visual labels including colloidal metallic particles such as gold, colloidal non-metallic particles such as selenium, dyed or colored particles such as a dyed plastic or a stained microorganism, organic polymer latex particles and liposomes or other vesicles containing directly visible substances; and the like.

The selection of a particular label is not critical to the present invention, but the label will be capable of generating a detectable signal either by itself, such as a visually detectable colored organic polymer latex particle, or be instrumentally detectable, such as a fluorescent compound, or be detectable in conjunction with one or more additional signal producing components, such as an enzyme/substrate signal producing system. A variety of different conjugates can be formed by varying either the label or the specific binding member component of the conjugate; it will be appreciated by one skilled-in-the-art that the choice involves consideration of the analyte to be detected and the desired means of detection.

"Signal producing component" refers to any substance capable of reacting with another assay reagent or with the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be reacted with the label to generate a detectable signal, e.g., when the label is an enzyme, amplification of the detectable signal is obtained by reacting the enzyme with one or more substrates or additional enzymes and substrates to produce a detectable reaction product.

In an alternative signal producing system, the label can be a fluorescent compound where no enzymatic manipulation of the label is required to produce the detectable signal. Fluorescent molecules such as fluorescein, phycobiliprotein, rhodamine and their derivatives and analogs are suitable for use as labels in such a system.

In a preferred embodiment of the present invention, a visually detectable label is used as the label component of the conjugate, thereby providing for the direct visual or instrumental readout of the presence or amount of the analyte in the test sample without the need for additional signal producing components at the detection sites. Suitable materials for use are colloidal metals, such as gold, and dyed or colored particles. Non-metallic colloids, such as colloidal selenium, tellurium and sulfur particles may also be used. Visually detectable organic polymer latex particles may also be used as labels and are disclosed in coowned and copending U.S. Pat. application Ser. No. 248,858, filed Sep. 23, 25 1988, herein incorporated by reference.

"Solid phase" refers to any solid material to which analyte, analyte complexes or assay reagents become bound and which can be separated from unreacted assay reagents, test sample or test solutions. For example, the solid phase may involve beads, magnetic particles, latex particles, test tubes, microtiter plates or any other solid material. In preferred embodiments, the solid phase is any suitable chromatographic, bibulous, porous, isotropic or capillary material, hereinafter referred to as porous material, which forms the basis of the test device. The assay device of the present invention can have many configurations, several of which are dependent upon the material chosen for the solid phase. For example, the assay device can include a solid phase material configured for use in a layered flow-through assay device, a chromatographic column, a dipstick or a test strip.

It will be appreciated by one skilled-in-the-art that a test strip device can be made of more than one material (e.g., different zones or sites can be made of different materials) and a flow-through device can have more than one layer, wherein different layers can be made of different materials, so long as the multiple materials or layers are in fluid-flow contact with one another thereby enabling the passage of test sample between the materials or layers. Fluid-flow contact permits the passage of at least some components of the test sample between the zones or layers of the device. Fluid-flow is preferably uniform along the contact interface between the different zones or layers.

In a flow-through device of the present invention, a blocking layer may be present between individual capture sites such that the presence or amount of label immobilized at each site can be separately detected and/or measured without an interfering signal from the other sites. It will also be appreciated that those zones or layers of the device which contain an assay reagent can be separated by zones or layers which do not contain reagents so long as each of the zones, layers or reagent sites are in continuous fluid-flow contact; this is referred to as the indirect fluid-flow contact of reagent containing zones or layers. To simplify the disclosure hereinafter, the test device of the present invention will be described principally as comprising a test strip structure containing at least the immobilized binding reagents necessary for the performance of the specific binding assay.

"Capture reagent" refers to a specific binding member that is attached within or upon a portion of the solid phase to form a "capture site". The method of attachment is not critical to the present invention. The capture reagent is selected to bind the analyte, the conjugate or a complex thereof. In preferred embodiments, the capture reagent binds to the analyte for the completion of a sandwich complex. The capture reagent can be chosen to directly bind the analyte or indirectly bind the analyte by binding to an ancillary specific binding member which is bound to the analyte. In addition, the capture reagent may be immobilized on the solid phase before or during the performance of the assay by means of any suitable attachment method.

Typically, the capture site of the present invention is a delimited or defined portion of the solid phase such that the specific binding reaction of the capture reagent and analyte is localized or concentrated in a limited site, thereby facilitating the detection of label that is immobilized at the capture site in contrast to other portions of the solid phase. The capture reagent can be applied to the solid phase by dipping, inscribing with a pen, dispensing through a capillary tube or through the use of reagent jet-printing or other techniques. In addition, the capture site can be marked, for example with a dye, such that the position of the capture site upon the solid phase can be visually or instrumentally determined even when there is no label immobilized at the site.

"Ancillary specific binding member" refers to any member of a specific binding pair which is used in the assay in addition to the specific binding members of the conjugate or capture reagent. One or more ancillary specific binding members can be used in an assay. For example, an ancillary specific binding member can be capable of binding the conjugate to the analyte of interest, in instances where the analyte itself could not directly attach to the conjugate. The ancillary specific binding member can be incorporated into the assay device or it can be added to the device as a separate reagent solution.

"Analyte derivative" refers to any substance whose concentration in the test sample or assay reaction mixture is directly proportional to the analyte concentration. For example, the derivative may be a complex of the analyte and an ancillary specific binding member which in turn binds to an affixed member. As another example, the derivative can be a reaction product formed in stochiometric relationship to the analyte concentration, wherein the reaction product binds to an affixed member. Thus, an analyte derivative is any substance quantitatively related to analyte concentration.

Assay Methods

While the methods and devices of the present invention may be applied to any suitable specific binding pairs, the following examples will typically refer to antibody/antigen specific binding pairs in order to simplify the description.

One embodiment of the present invention involves an antibody/antigen sandwich assay format as illustrated in FIG. 1. A reaction mixture is made by contacting the test sample suspected of containing the analyte (Ag) with a predetermined amount of labeled anti-analyte antibody (Ab*) and a different amount of an unlabeled anti-analyte antibody (Ab) as the calibration reagent. In order to produce a detectable analyte complex, the test sample analyte must be present at a concentration sufficient to bind the available calibration reagent as well as the excess labeled anti-analyte antibody. The labeled anti-analyte antibody and calibration reagent bind to the analyte in the reaction mixture to form Ag-Ab* and Ab-Ag-Ab* complexes.

Figure 2:
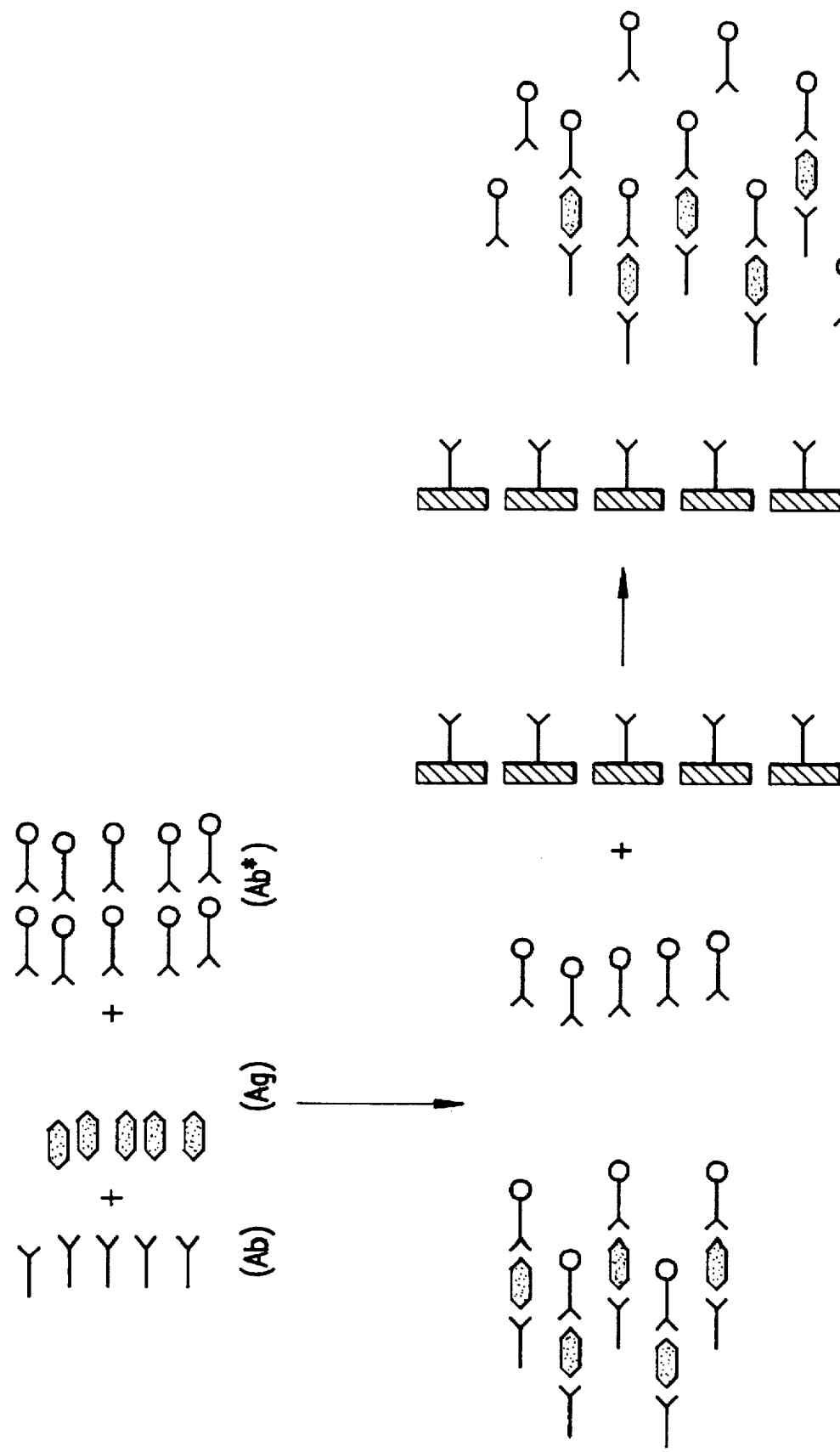
FIG. 2 depicts an antibody/antigen sandwich assay in accordance with the present invention wherein analyte is not present at a minimum amount to be detected.

The reaction mixture is then contacted with an immobilized antibody (|Ab) that is capable of binding to the unblocked Ag-Ab* complex to form an immobilized |Ab-Ag-Ab* complex. The calibration reagent is chosen such that the immobilized antibody is unable to bind to the Ab-Ag-Ab* complex. The immobilized complex can then be separated from the test sample, as well as the non-immobilized assay reagents and complexes, prior to the detection of the label. If the analyte is present at a level above such minimum concentration, then labeled analyte complex is formed and detected. As the amount of analyte in the test sample increases, the formation of labeled analyte complex increases, and the immobilization of labeled analyte complex on the solid phase increases. If the analyte is not present in a minimum threshold amount, then substantially all of the analyte binding sites are filled by the labeled anti-analyte antibody and the calibration reagent, thereby inhibiting the immobilization and separation of the labeled analyte complex. This event is illustrated in FIG. 2.

Figure 3:
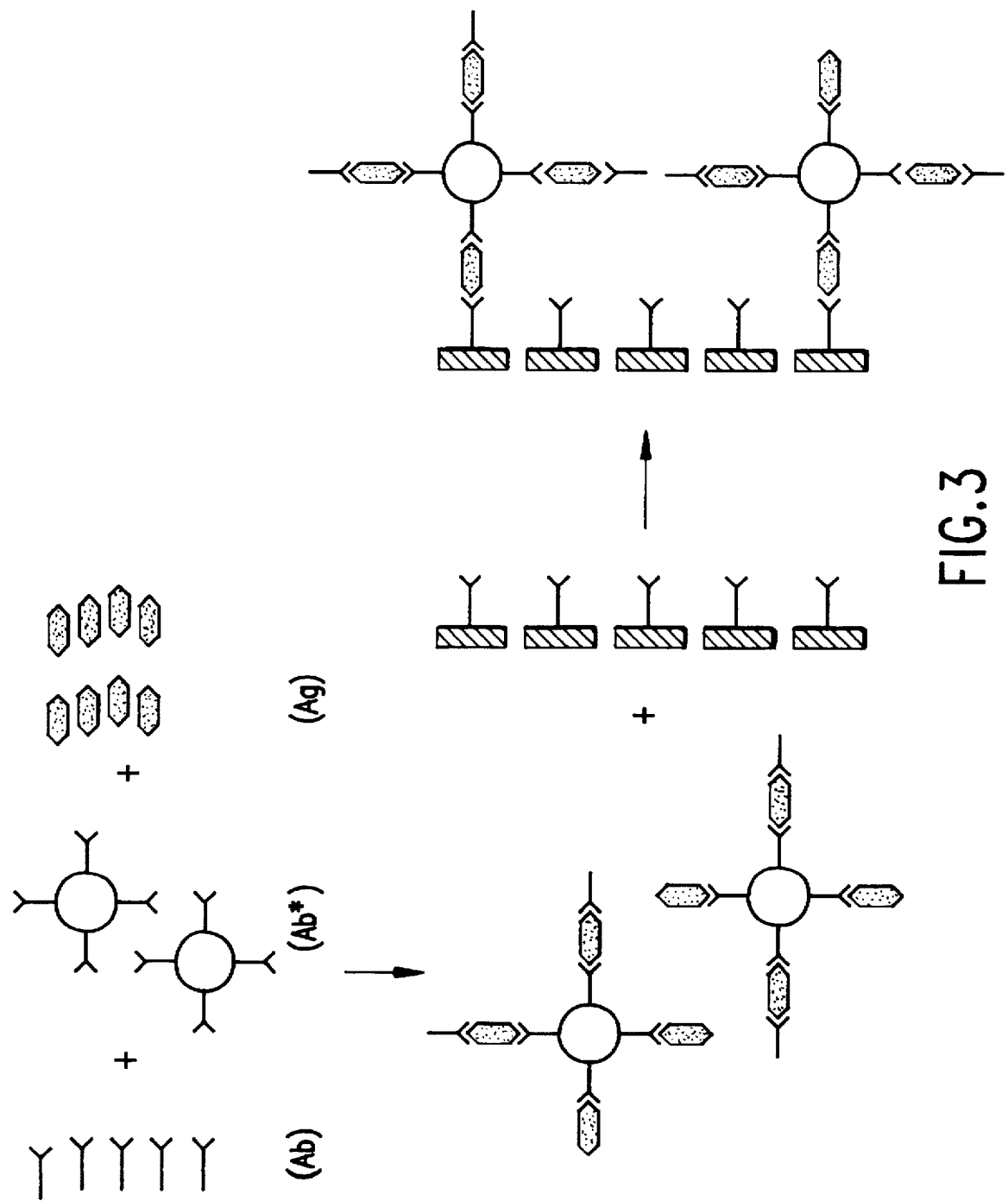
FIG. 3 depicts an sandwich assay using a visually detectable particle as the label, wherein a plurality of analyte-specific binding members are conjugated to the surface of the particle in accordance with the present invention.
Figure 4:
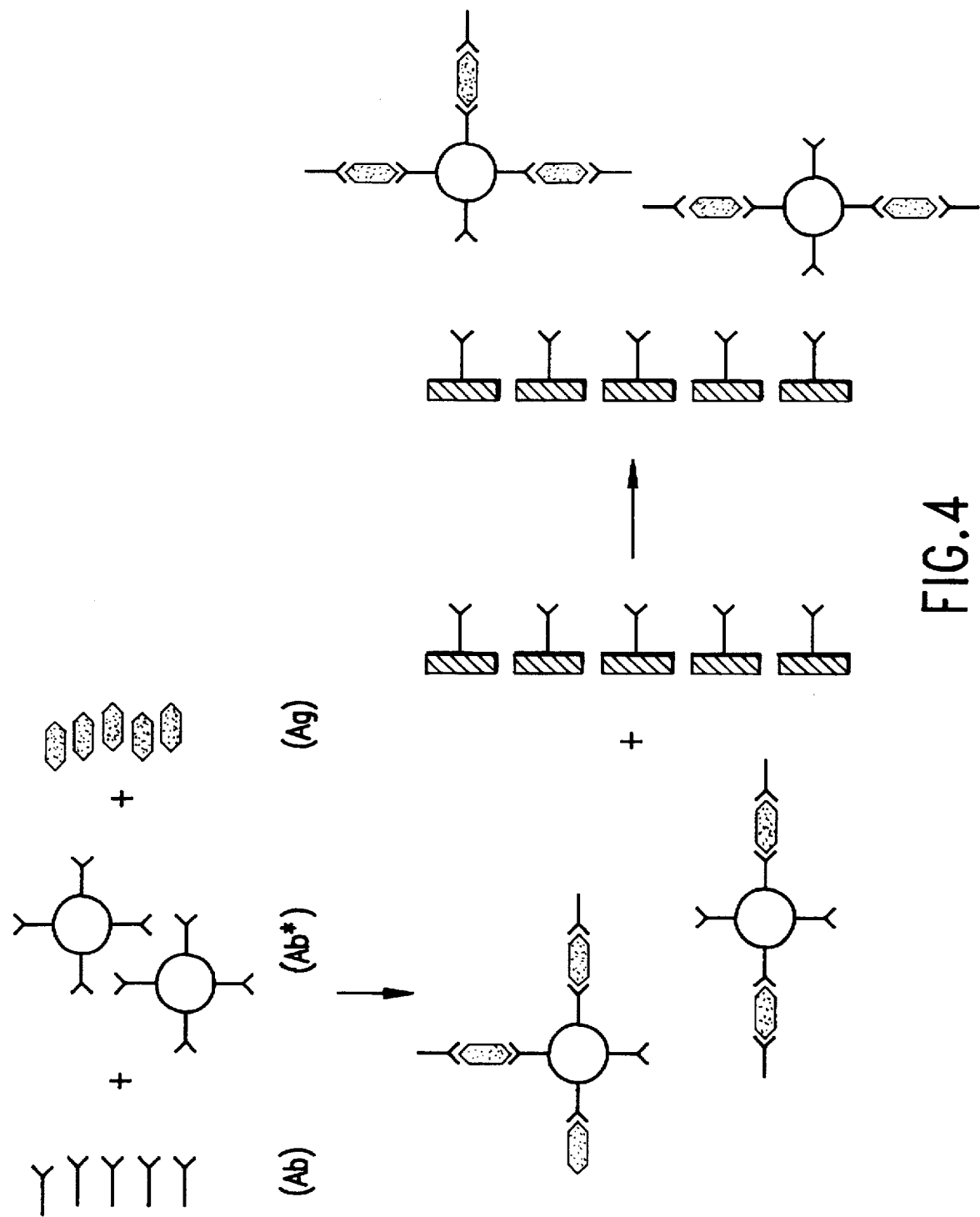
FIG. 4 depicts the assay in accordance with FIG. 3 wherein analyte is not present at a minimum amount to be detected.
Figure 5E:
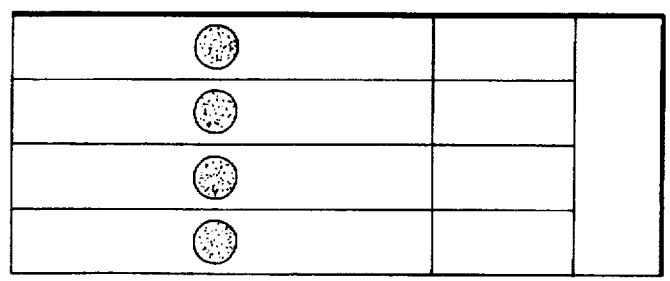
FIG. 5 depicts a multiple strip assay device in accordance with the present invention.
Figure 5D:
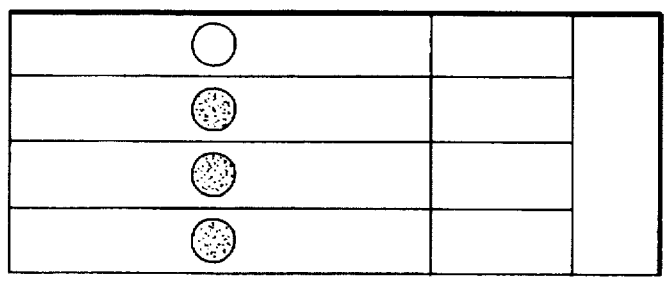
Figure 5C:
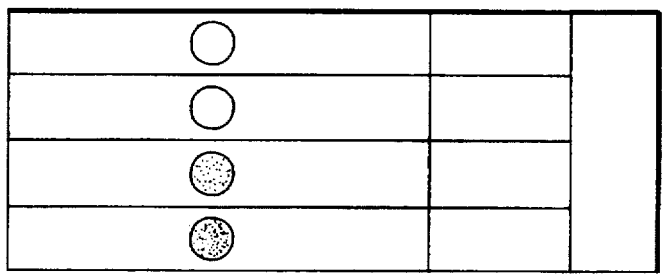
Figure 5B:
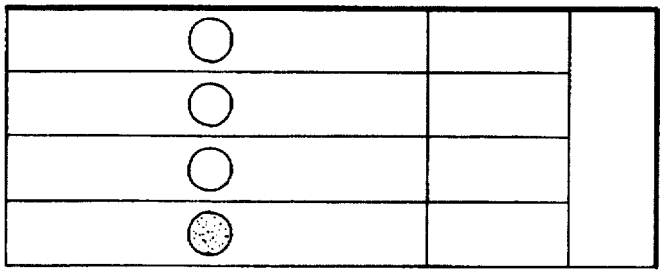
Figure 5A:
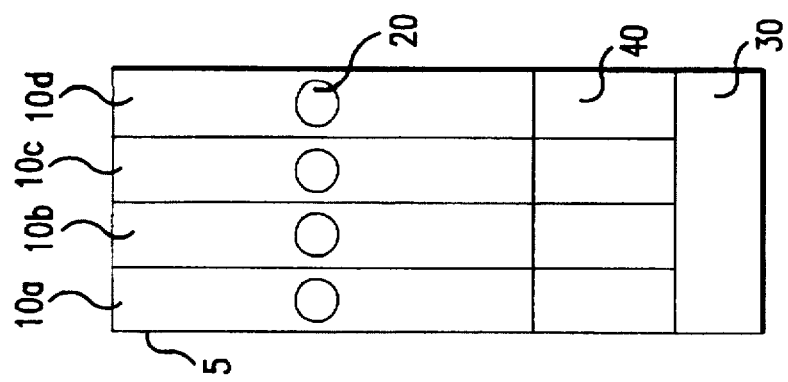

An alternative embodiment is illustrated in FIG. 3. In this method, a visually detectable particle is used as the label, wherein a plurality of analyte-specific binding members are conjugated to the surface of the particle. A reaction mixture is made by contacting the test sample suspected of containing the analyte (Ag) with a predetermined amount of antibody-coated detectable label (Ab*) and a different amount of an unlabeled calibration reagent (Ab). The antibody-coated detectable label and calibration reagent bind to the analyte in the reaction mixture to form a labeled complex. The reaction mixture is then contacted with an immobilized antibody (|Ab) that is capable of binding to the unblocked Ag binding sites to form an immobilized |Ab-Ag-Ab* complex. The immobilized complex can then be separated from the test sample prior to the detection of the label. If there is more calibration reagent present than there is analyte, then the complexes will not attach to the solid phase as illustrated in FIG. 4.

In yet another embodiment, the calibration reagent is an analyte-analog which binds to the conjugate but which prevents the conjugate from becoming indirectly bound to the capture reagent. As described above, suitable analyte-analogs include a modified analyte as well as a fragmented or synthetic portion of the analyte molecule, so long as the analyte-analog has at least one epitopic site in common with the analyte of interest.

Assay Device

The assay device of the present invention is any suitably porous material, through which a solution or fluid containing the analyte can pass. The solution can be pulled or pushed through the solid phase by suction, hydraulic, pneumatic, hygroscopic or capillary forces, or by a combination thereof. Alternative assay devices include, but are not limited to, a conventional chromatographic column, an elongated strip of material wherein the fluid-flow is substantially linear, or a sheet wherein the fluid-flow is linear or radial. As described above, if a flow-through device is used, a blocking layer is generally present between any multiple capture sites such that the presence or amount of label immobilized at each site can be separately detected and/or measured without the occurrence of an interfering signal. For example, a suitable blocking layer component for use with chromogenic or colloidal particle labels can include any opacifying material which will inhibit the signal of one site from being detectable at the other readout site or sites. While the novel assay methods of the present invention may be applied to any suitable device format, the following examples will typically refer to teststrip devices in order to simplify the description.

Natural, synthetic, or naturally occurring solid phase materials that are synthetically modified, can be used and include: papers (fibrous) or membranes (microporous) of cellulose materials such as paper, cellulose, and cellulose derivatives such as cellulose acetate and nitrocellulose; fiberglass; cloth, both naturally occurring (e.g., cotton) and synthetic (e.g., nylon); porous gels such as silica gel, agarose, dextran, and gelatin; porous fibrous matrixes; starch based materials, such as Sephadex® brand cross-linked dextran chains; ceramic materials; olefin or thermoplastic materials including films of polyvinyl chloride, polyethylene, polyvinyl acetate, polyamide, polycarbonate, polystyrene, copolymers of vinyl acetate and vinyl chloride and combinations of polyvinyl chloride-silica; and the like. The solid phase material should not interfere with the production of a detectable signal. If a strip or sheet is used, then the material should have a reasonable inherent strength, or strength can be provided by means of an additional supplemental support material.

One preferred solid phase material is nitrocellulose. Especially when a membranous solid phase material is used, the test sample, competitive reagent and/or conjugate may be mixed prior to initiating fluid-flow through the solid phase to obtain a controlled, reproducible binding reaction between the analyte and the assay reagents. In alternative test devices, a premixing application pad may be included, wherein the pad contains the conjugate or a mixture of the conjugate and the unlabeled competitive specific binding member. The material of the application pad should be chosen for its ability to premix the test sample with the assay reagents. If nitrocellulose is used as the solid phase, then a hydrophilic polyethylene material or glass fiber filter paper are appropriate application pad materials. Alternatively, if a solid phase material such as glass fiber filter paper is used, then one or more assay reagents can be reversibly immobilized on the strip either at the sample application site or at another site upstream of the capture site. Other reagents which can be contained in the application pad include, but are not limited to, ancillary specific binding members, test sample pretreatment reagents and signal producing components. The isolation of assay reagents in the application pad also keeps interactive reagents separate and facilitates the manufacturing process.

An application pad can be made of any material from which the test sample can pass to the test strip. Materials preferred for use in the application pad include porous polyethylene material or pads and glass fiber pads or filter paper. The material must also be chosen for its compatibility with the analyte and assay reagents.

The particular dimensions of the solid phase will be a matter of convenience and will depend upon the size of the test sample involved, the assay protocol, the label detection means, the measurement means, and the like. For example, the dimensions may be chosen to regulate the rate of fluid migration as well as the amount of test sample to be imbibed by the solid phase.

It is not critical to the present invention that the capture reagent be bound directly to the solid phase. The specific binding member can be attached to another material wherein that material is physically entrapped or retained and immobilized within the solid phase by a physical, chemical or biochemical means. For example, an analyte-specific binding member can be attached to insoluble microparticles which are subsequently retained by the solid phase. The means of attaching a reagent to the microparticles encompasses both covalent and non-covalent means. It is generally preferred that the capture reagent be attached to the microparticles by covalent means. By "retained" is meant that the particles, once on the solid phase, are not capable of substantial movement to positions elsewhere within the solid phase material. The particles can be selected by one skilled-in-the-art from any suitable type of particulate material including materials composed of polystyrene, polymethylacrylate, polyacrylamide, polypropylene, latex, polytetrafluoroethylene, polyacrylonitrile, polycarbonate, glass or similar materials.

The size of the particles may vary depending upon the type of solid phase material used as well as the type of material from which the particle is made. For example, in a glass fiber assay device, glass and polystyrene particles should be of sufficient size to become entrapped or immobilized in the pores of the solid phase material and not move when confronted by the passage of test sample or other fluids. In the same glass fiber matrix, much smaller latex particles can be used because the latex particles unexpectedly affix themselves to the glass fibers by an unknown mechanism. Thus, unlike the pore size dependent glass and plastic particles, the latex particles are pore sized independent so that lot-to-lot variations in pore size of the solid phase will not adversely affect the performance of the device.

In yet another embodiment, the particles may be magnetic or magnetizable particles which are separated from the test solution upon the application of a magnetic field. In yet a further embodiment, separation can be performed by the use of a charged capture reagent and an oppositely charged solid phase material, for example a conjugate of a polymeric anion and an analyte specific binding member together with a solid phase bearing a polymeric cationic substance. Thus, it will be appreciated by those skilled in the art that the method of separation is not critical to the present invention.

Predetermined amounts of signal producing components and ancillary specific binding members can be incorporated within the device, thereby avoiding the need for additional protocol steps or reagent additions. Thus, it is also within the scope of this invention to provide more than one reagent to be immobilized within the solid phase. For example, to slow or prevent the diffusion of the detectable reaction product in an enzyme/substrate signal producing system, the substrate can be immobilized by direct attachment to the test strip by methods well-known in the art, or the substrate may be immobilized by being covalently bound to insoluble microparticles which have been deposited in and/or on the test strip.

The capture reagent may be provided in a single capture or detection site or in multiple sites on or in the test strip. The capture reagent may also be provided in a variety of configurations to produce different detection or measurement formats. For example, the capture reagent can be deposited to form discrete binding sites which are substantially smaller than the area of the entire test strip.

Alternatively, the capture reagent can be distributed over a large portion of the test strip in a substantially uniform manner to form the capture site. The extent of signal production along the length of the capture site is related to the amount of analyte in the test sample. The amount of analyte can be determined by a comparison of the length or distance of the resulting signals to those observed for calibrated standards of analyte or other calibration scale provided with the device by the manufacturer.

Alternative embodiments include, but are not limited to: distributing the reagents in a gradient pattern, i.e., a lesser amount of reagent at the downstream end than at the upstream end of the capture site; distributing the appropriate assay and control reagents to form patterns including numerals, letters, dots and symbols such as "+/−", "%" or the like; or distributing the reagents as a series of parallel bars which are spaced from about the proximal end, e.g., the sample application end of the strip, to about the distal end, thereby creating a ladder-like capture site configuration; or distributing the reagents as sequential rings surrounding a central test sample or test solution application site on a sheet-like device.

The various signal display formats or patterns described above can also incorporate assay controls to confirm the efficacy of the assay reagents or device, the completion of the assay or the proper sequence of assay steps. It is also within the scope of this invention to have a reagent, at the distal end of a test strip device, which indicates the completion of a binding assay (i.e., an end of assay indicator). For example, the end of the assay may be shown by the indicator's changing color upon contact with the test solution, wicking solution or a signal producing component. Reagents which would change color upon contact with an aqueous test solution include the dehydrated transition metal salts, such as $CuSO_4$, $Co(NO_3)_2$, and the like. The pH indicator dyes can also be selected to respond to the pH of the buffered wicking solution. For example, phenolphthalein changes from clear to intense pink upon contact with a wicking solution having a pH range between 8.0–10.0.

A test sample can be contacted to the test strip by applying the test sample to an application site or by immersing the application site in the test sample. In a sheet-like device having radial capture sites, the sample is applied to a central application site. In a test strip or column, the sample can be applied to any portion of the strip which is upstream of the capture site, or the application site can be the capture site. Prior to contacting the sample to the solid phase, the sample can also be mixed with additional reagents such as the conjugate, buffers or wicking reagents (i.e., reagents which facilitate the travel of the test sample through the solid phase). In a further embodiment, the test sample can be applied to one portion of the test strip, upstream of the capture site, with one or more of the additional reagents being applied to yet another portion of the test strip upstream of the test sample application site.

The present invention can be further modified by the addition of a filtration means. The filtration means can be a separate material placed above the application site or application pad, or placed between the application pad and the test strip. Alternatively, the material of the application site or pad can be chosen for its filtration capabilities. The filtration means can include any filter or trapping device used to remove particles above a certain size from the test sample. For example, the filter means can be used to remove red blood cells from a sample of whole blood, such that plasma is the fluid transferred to the test strip. Optionally, the filter means can include a reagent or reagents to remove particles or interferents from the test sample.

Another embodiment of the present invention involves the use of an additional zone, layer or layers of material placed between the application site or pad and the remaining test strip to control the rate of flow of the test sample from the application site or pad to the test strip. Such flow regulation is preferred when an extended incubation period is desired for the reaction of the test sample and the reagent(s) at the application site or pad. Alternatively, such a zone or layer can contain an additional assay reagent(s) which is preferably isolated from the application site or pad reagents until the test sample is added, or it can serve to prevent unreacted sample or assay reagents from passing to the test strip.

In yet another embodiment, the device can include an absorbent material downstream from the capture site or sites. It will be appreciated that the absorbent material can serve to increase the amount of test sample which passes through the capture site on the solid phase.

When small quantities of non-aqueous or viscous test samples are applied to the device, it may be necessary to employ a wicking solution, preferably a buffered wicking solution, to facilitate the travel of the reagent(s) and test sample through the device. When an aqueous test sample is used, a wicking solution generally is not necessary but can be used to improve flow characteristics or adjust the pH of the test sample.

In one assay device of the present invention, the test sample is combined with a conjugate, such as a labeled anti-analyte antibody, and a calibration reagent, thereby forming a test solution. The test solution is contacted to a solid phase device, such as a test strip. The strip includes an application site to which the test solution is contacted and a capture site to which is affixed a capture reagent (e.g., an immobilized analyte-specific binding member) that is capable of binding with the analyte and thereby immobilizing the analyte and analyte complexes. In an alternative embodiment, the labeled anti-analyte antibody and/or the calibration reagent are present on the teststrip. The reagents may be in the application site or in any potion of the strip that is upstream of the capture site. By incorporating all of the reagents into or on the solid phase test device, the assay is substantially self-performing once the test solution is contacted to the assay device. In those assay methods involving a label which is not detectable by itself, the solid phase is also contacted to any remaining members of a signal producing system that were not included with the test solution or were not present on the solid phase.

The binding of the labeled antibody and unlabeled calibration reagent to the analyte results in the formation of analyte complexes. By using an appropriate amount of calibration reagent, a predetermined minimum level of analyte must be present in the test sample before a sufficient amount of immobilizable analyte/conjugate complex is formed and captured at the capture site. Thus, more than this predetermined minimum concentration of analyte must be present in the test sample before a detectable signal will be produced at the capture site.

In a preferred assay device, two or more strips are used wherein each contains a different predetermined amount of the calibration reagent such that different levels of analyte can be detected in the test sample. A representative device is depicted in FIG. 5 (a–e). The device (5) includes four parallel strips (10a–10d) each having a capture site (20), and each strip containing the same fixed amount of labeled anti-analyte antibody in the application pad (30) and a different amount of the calibration reagent in a calibration reagent zone (40). Alternatively, a device may be constructed wherein each strip has a separates application pad. Because of the differing amounts of calibration reagent, each capture site will display a detectable signal only if the amount of analyte present in the sample is greater than the amount to which substantially all of the calibration reagent will bind. For example, if strip 10a contains concentration

|A| of calibration reagent, then concentration |A+x| of analyte must be present to obtain the immobilization of a detectable amount of analyte (x) or analyte complex at the capture site. Similarly, Strips 10b through 10d may individually contain concentrations |B|, |C| and |D| of calibration reagent, respectively, and require concentrations |B+x|, |C+x| and |D+x| of analyte, respectively, to obtain the immobilization of a detectable analyte complex at each respective capture site. Thus, a device can be made which allows the semiquantitative detection of analyte concentrations within a given range. FIG. 3a depicts such a device before use. FIG. 3b depicts a device wherein the test sample contains at least concentration |A+x| of analyte. FIG. 3c depicts a device wherein the test sample contains at least concentration |B+x| of analyte. FIG. 3d depicts a device wherein the test sample contains at least concentration |C+x| of analyte and FIG. 3e depicts a device wherein the test sample contains at least concentration |D+x| of analyte.

The assay devices of the present invention may also include an ancillary specific binding members as discussed above. One or more ancillary specific binding members can be placed at appropriate locations in or on the device, or be added separately thereto, to complete the binding of analyte, conjugate or analyte/conjugate complex at the capture site. The ancillary specific binding members can include complexes formed from two or more specific binding members.

The present invention further provides kits for carrying out binding assays. For example, a kit according to the present invention can include the assay device with its incorporated reagents, and can optionally include a wicking solution and/or test sample pretreatment reagent as described above. Alternatively, the kit can include the solid phase device containing the immobilized binding member together with containers of conjugate and unlabeled calibration reagent. Other assay components known to those skilled-in-the-art, such as buffers, stabilizers, detergents, non-specific binding inhibitors, bacteria inhibiting agents and the like can also be present in the assay device and wicking solution.

EXAMPLES

The following example is given by way of illustration only and should not be construed as limiting the scope of the invention as based upon this disclosure. Many variations on the present invention will become obvious to those of ordinary skill-in-the-art.

Human Chorionic Gonadotropin (hCG) Assay a. Conjugate

The conjugate involved a monoclonal anti-hCG antibody conjugated with a colloidal gold label. The colloidal gold suspension was adjusted to pH 6.6 with potassium carbonate, and the monoclonal antibody was added (3µg/ml). After a one minute incubation, 0.3% bovine serum albumin was added to block the conjugate and thereby inhibit nonspecific binding. The resulting conjugate was combined with 2% casein in Tris-buffered saline (50 mM Tris, 0.9% sodium chloride, pH 7.4) to facilitate the movement of the conjugate in the test strip.

b. Test strip

A nitrocellulose strip (5µm pore size) was used as the solid phase. Strips of nitrocellulose (three by five millimeters) were prepared, and anti-hCG polyclonal antibody was applied to the membrane in a localized site to form the capture site. Four strips were assembled to produce one assay device.

c. Assay protocol

The conjugate was divided into four different tubes, and various amounts (0, 2, 4 and 8µg/ml) of free monoclonal anti-hCG antibody were added to the tubes as a calibration reagent. An aliquot of each mixture was placed into a reaction well together with an hCG test sample. Thus, the conjugate competed with the free antibody calibration reagent for binding to the analyte. After incubation at room temperature for thirty seconds, the teststrip device was contacted with the test solution. The test solution was contacted to the bottom of the teststrips, and the test solution was transported through the membrane by capillary action. Five minutes later, the detectable signal at the capture site could be read. The results are presented in Table 1. As the amount of hCG present in the test sample was increased, the amount of labeled antibody/hCG complex that was formed also increased, even in the presence of increased amounts of calibration reagent.

TABLE 1

| Concentration of hCG (mIU/ml) | Number of capture sites observed in the 4 strip set |
|---|---|
| 20 | 1 |
| 40 | 2 |
| 100 | 3 |

It will be appreciated by those skilled-in-the-art that the concepts of the present invention are applicable to various types of assay configurations, analytes, labels and solid phase materials. Thus, the present inventive concepts can be applied to many other signal producing assays. The embodiments described and the alternative embodiments presented are intended as examples, rather than as limitations, of assay devices containing a self1 confirming assay component. Thus, the description of the invention is not intended to limit the invention to the particular embodiments disclosed, but it is intended to encompass all equivalents and subject matter within the scope of the invention as described above and as set forth in the following claims.

What is claimed is:

1. A multizone test device for semiquantitatively determining the presence of at least a predetermined minimum concentration of an analyte in a test sample, said device comprising:

a strip of porous material, said strip comprising a reagent zone and a capture site, said reagent zone being upstream from said capture site, a soluble conjugate comprising a labeled analyte-specific binding member which binds the analyte to form a labeled analyte complex, said soluble conjugate contained in said reagent zone, a capture reagent comprising an unlabeled specific binding member attached to said porous material, wherein said capture reagent binds the labeled analyte complex to form an immobilized labeled analyte complex, and a soluble calibration reagent comprising a n unlabeled specific binding member which blocks the binding of the analyte to said capture reagent, thereby controlling the proportion of the analyte that binds to said capture reagent such that the analyte in the test sample must exceed a minimum concentration before said immobilized labeled complex is formed, said calibration reagent contained in said reagent zone, said capture reagent being immobilized at said capture site wherein said immobilized labeled complex is separated from the test sample, and wherein the presence of label associated with said immobilized labeled complex is detected to determine the presence of at least a predetermined minimum concentration of an analyte in the test sample.

2. The device according to claim 1, wherein said reagent zone comprises at least two reaction zones, a first reaction zone containing said calibration reagent and a second reaction zone containing said conjugate.

3. The device according to claim 1, wherein said calibration reagent is selected from the group consisting of an analyte-specific binding member and an analyte-analog.

4. The device according to claim 3, wherein said analyte-analog is a fragment of an analyte molecule.

5. The device according to claim 3, wherein said analyte-analog is a synthetic analyte molecule.

6. The device according to claim 1, wherein said calibration reagent is an antiidiotypic antibody.

7. The device according to claim 1, wherein said conjugate is a visually detectable particle coated with more than one analyte-specific binding member.

8. A multizone test device for semiquantitatively determining the presence of at least a predetermined minimum concentration of an analyte in a test sample, said device comprising:

a strip of porous material, said strip comprising a reagent zone and a capture site, said reagent zone being upstream from said capture site, a soluble conjugate comprising a labeled analyte-specific binding member which binds the analyte to form a labeled analyte complex, said soluble conjugate contained in said reagent zone, a capture reagent comprising a n unlabeled specific binding member attached to said porous material, wherein said capture reagent binds the labeled analyte complex to form an immobilized labeled analyte complex, and a soluble calibration reagent comprising an unlabeled specific binding member which blocks the binding of the analyte to said conjugate, thereby controlling the proportion of said labeled analyte complex that binds to said capture reagent such that the analyte in the test sample must exceed a minimum concentration before said immobilized labeled complex is formed, said calibration reagent contained in said reagent zone, said capture reagent being immobilized at said capture site wherein said immobilized labeled complex is separated from the test sample, and wherein the presence of label associated with said immobilized labeled complex is detected to determine the presence of at least a predetermined minimum concentration of an analyte in the test sample.

9. The device according to claim 8, wherein said calibration reagent and said labeled analyte-specific binding member are the same specific binding members.

* * * * *